United States Patent [19]
Yoshida et al.

[11] Patent Number: 5,579,769
[45] Date of Patent: Dec. 3, 1996

[54] COUPLING MEDIUM FOR PROBE OF ULTRASONOGRAPH

[75] Inventors: Katsunori Yoshida; Toshio Yanaki; Michihiro Yamaguchi, all of Yokohama, Japan

[73] Assignee: Shiseido Company, Ltd., Tokyo, Japan

[21] Appl. No.: 284,420

[22] PCT Filed: Dec. 2, 1993

[86] PCT No.: PCT/JP93/01759

§ 371 Date: Aug. 2, 1994

§ 102(e) Date: Aug. 2, 1994

[87] PCT Pub. No.: WO94/12105

PCT Pub. Date: Jun. 9, 1994

[30] Foreign Application Priority Data

| Dec. 2, 1992 | [JP] | Japan | 4-349847 |
| Jan. 8, 1993 | [JP] | Japan | 5-018046 |
| Jan. 8, 1993 | [JP] | Japan | 5-018047 |
| Sep. 9, 1993 | [JP] | Japan | 5-248836 |
| Sep. 24, 1993 | [JP] | Japan | 5-238175 |
| Oct. 29, 1993 | [JP] | Japan | 5-294596 |

[51] Int. Cl.$^6$ ............................................. A61B 8/00
[52] U.S. Cl. ............................... 128/660.01; 528/60
[58] Field of Search .................. 128/660.01, 667.02; 528/60

[56] References Cited

U.S. PATENT DOCUMENTS

| 4,505,757 | 3/1985 | Kojima et al. | 127/36 |
| 4,905,700 | 3/1990 | Wokolek et al. | 128/660.01 |
| 4,960,953 | 10/1990 | Shikinami et al. | 528/60 |
| 5,039,774 | 8/1991 | Shikinami et al. | 528/60 |
| 5,071,602 | 12/1991 | Nambu et al. | 128/653.5 |

Primary Examiner—Francis Jaworski
Attorney, Agent, or Firm—Foley & Lardner

[57] ABSTRACT

A coupling medium for a probe of an ultrasonograph comprising a gel composed of β-1,3 glucan as the main component, or a gel obtained by high pressure treatment or chemical cross-linking of the same, or a gel containing β-1,3 glucan and a complex forming compound capable of forming a complex with β-1,3 glucan.

19 Claims, 6 Drawing Sheets

COUPLING MEDIUM FOR PROBE OF ULTRASONOGRAPH

The present invention relates to coupling medium for a probe of an ultrasonograph.

BACKGROUND ART

In recent years, various methods have been tried to treat diseases of the internal organs, without applying major surgery, so as to lighten the physiological load on the patient and improve the progress in recuperation. Also, even if an abdominal operation is to be performed, the detailed determination of the state of diseased areas before surgery and determination of the internal state without having to cut open the organ surface during surgery would give very meaningful information at the time of actual surgery. To reply to these needs, in recent years, ultrasonography has developed and remarkably spread. The accuracy of the diagnosis using the ultrasonography before surgery has been extremely helpful in improving results of surgery in recent years. In particular, remarkable improvements have been made in the ability to diagnose diseases of the thyroid glands by the combination of the ultrasonography method and diagnosis of cells obtained by centesis and suction.

When trying to observe the internal state by placing the probe of the ultrasonograph directly on the body surface or organ surface, however, it is difficult to obtain a clear image in the region within several centimeters from the surface due to the nature of the ultrasonograph. Further, the actual body and organ surfaces are not flat, but have characteristic curves and unevenness, so it is impossible to bring an inflexible probe which maintains a certain shape into close contact with the desired location. That is, when air is present between the body and probe, the rate of propagation of the ultrasonic waves remarkably decreases, and an accurate image cannot be formed on the screen of the diagnostic apparatus.

To solve the above-mentioned problems, it is effective to interpose a suitable spacer (i.e., coupling medium) between the probe and body. The coupling medium is preferably made is the form of a sheet-like shape and is sandwiched between the probe and, for example, the body surface at the time of diagnosis or is formed into a suitable shape capable of being used by attaching to the probe directly or with a fitting. Such a coupling medium is required to have a suitable flexibility and mechanical strength and improved acoustic property (i.e., a low rate of attenuation etc.). For example, Japanese Unexamined Patent Publication (Kokai) No. 55-63636 discloses a specific water-containing polymer gel. The gel disclosed therein, however, has problems such as an insufficient mechanical strength or a large attenuation of sound waves. Various efforts have been made to deal with this problem. For example, there are known a polyvinyl alcohol based polymer gel (Japanese Unexamined Patent Publication (Kokai) No. 62-298342 and Japanese Examined Patent Publication (Kokoku) No. 2-46211), a highly water absorbing resin (Japanese Unexamined Patent Publication (Kokai) No. 4-53544), and various organic and inorganic polymers (Japanese Examined Patent Publication (Kokoku) No. 2-21252).

These various proposed polymer gels, however, also suffer from various problems. Namely, media using synthetic polymers suffer from the danger of all or part of the gel entering and remaining in the living body at the time of centesis or surgery. Thus, there are apprehensions over the toxicity of the gel itself or the residual monomers and therefore, there are problems in safety. Further, natural polymers and polyvinyl alcohol gels, which are considered highly safe, are not necessarily satisfactory in terms of their acoustic property (for example, the attenuation rate is high). To improve the acoustic property, it is necessary to increase the water content. However, when the water content is increased, there is the problem that the mechanical strength is decreased. Further, a polyvinyl alcohol gel tends to bleed water when pressure is applied and therefore is not suited as a gel for a probe used pressed against the human body or organ surface. Further, it is poor in sterilizability (that is, it completely melts and loses its original shape under heating at 121° C. by an autoclave, which is one of the most common method for sterilization). As a result, it is not yet commercialized. In view of this situation, development of a coupling medium for a probe which is safe and can be used even during centesis and surgery has been desired.

DISCLOSURE OF THE INVENTION

Accordingly, the object of the present invention is to resolve the above-mentioned problems in the prior art and to provide a coupling medium for a probe of a ultrasonograph which is free from problems in safety even if entering into the living body and is superior in acoustic property, mechanical strength, and sterilizabiity.

Other objects and advantages of the present invention will be clear from the following description.

In accordance with the present invention, there is provided a coupling medium for a probe of an ultrasonograph comprising a gel composed of β-1,3 glucan as a main component.

In accordance with there is also provided a coupling medium for a probe of an ultrasonograph obtained by subjecting a gel comprising β-1,3 glucan as a main component to a high pressure treatment.

In accordance with there is further provided a coupling medium for a probe of an ultrasonograph comprising a gel composed of β-1,3 glucan as a main component and having at least a portion of the gel chemically cross-linked.

In accordance with the present invention, there is further provided a coupling medium for a probe of an ultrasonograph comprising a gel composed of β-1,3 glucan as a main component and containing a complex forming compound which can form a complex with β-1,3 glucan.

Figure 1:
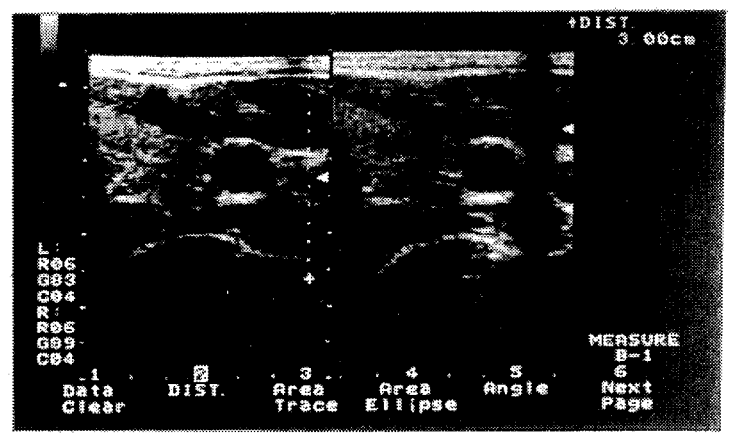
FIG. 1 is a photograph of an ultrasonographic image, in which the left side is the image of a human neck in the case of use of the probe coupling medium prepared in Example 1—1 and the right side is the image in the case of no use of the same.

Therefore, the present inventors engaged in intensive studies to solve the above problems and, as a result, found that by using, as a probe coupling medium, a gel composed of the natural polysaccharide curdlan or other β-1,3 glucan as a main component, or a gel comprising this gel subjected to high pressure treatment or at least partially cross-linked, or a gel containing β-1,3 glucan and a compound capable of forming a complex with β-1,3 glucan, all of the above-mentioned problems can be solved, whereby the present invention has been completed.

That is, the β-1,3 glucan used as a starting material in the present invention is extremely high in safety and has the property of gradually breaking down in the living body even if accidently remaining therein (see Yakugaku Zasshi, 110, (10) 869–875, 1990). Further, a gel prepared by adding a complex forming compound to the β-1,3 glucan can be sterilized by the most common sterilization apparatuses (autoclaves) or γ-ray irradiation and therefore is extremely superior as a coupling medium of a probe of an ultrasonograph, in particular, a probe coupling medium used during centesis and surgery.

The constitution of the present invention will be described in detail below.

The concentration of the β-1,3 glucan constituting the probe coupling medium according to the present invention is preferably 1 to 10% by weight, more preferably 2 to 5% by weight.

The probe coupling medium according to the present invention is a cross-linked high water content gel composed of β-1,3 glucan as a main component. The β-1,3 glucan is the generic name for polysaccharides having glucose as structural units and β-1,3 bonded main chains. Up to the present time, curdlan, scleroglucan, sclerotan, schizophyllan, lentinan, paramiron, calose, laminalan, and many others are known. Among these, curdlan is supplied to the market stably and at a relatively low price and is considered most suited as a material for a probe coupling medium.

Curdlan is described in the Nihon Shokuhin Kogyo Gakkaishi, Vol. 38, No. 8, 736–742 (1991) etc. and is one kind type of polysaccharides produced by microorganisms (*Alcaligenes faecalis* var. *myxogenes* or many strains of Agrobacterium and Rizobium) and only has D-glucose as a constituent saccharide. 99% or more of the glucoside bonds are β-1,3 bonds. Curdlan is insoluble in water, but dissolves in aqueous alkaline solutions of sodium hydroxide etc. A curdlan dispersion may be obtained as a homogeneous dispersion by adding water to a curdlan powder and vigorously agitating this by a high speed homogenizer or cutter mixer etc. or adding curdlan to warm water of about 55° C., while agitating manually or by a propeller type agitator etc., then cooling.

This aqueous dispersion forms a gel upon heating. The gel obtained by the heating may be classified into two main types depending on the treatment temperature. That is, there are a heat-irreversible gel obtained by heating at least at 80° C. and a heat reversible gel obtained by heating at about 60° C. and then cooling. These are respectively called a high set gel and low set gel.

It is also possible to prepare the gel without heating by dissolving the curdlan in an aqueous alkaline solution, allowing this to stand, and neutralizing by carbon dioxgen gas etc. or using a dialysis membrane to remove the sodium hydroxide. Further, it is possible to form a gel by adding, to the aqueous alkaline solution, calcium, magnesium ions, and other cations to form a cross-linked structure by the freed hydroxyl groups and cations.

β-1,3 glucans other than curdlan may also be made to form a gel in accordance with the above-mentioned method.

The method of manufacture of a probe coupling medium according to the present invention may be any method so long as a gel is obtained which is composed of curdlan or another β-1,3 glucan as a main component, has a water content of at least 80% by weight, and does not contain air bubbles. The method of manufacture is not particularly limited.

For example, describing two or three methods of preparation taking curdlan as an example, first the above-mentioned aqueous dispersion of curdlan is prepared.

The concentration of the curdlan is 1 to 10% by weight, preferably 2 to 5% by weight. Even if less than 1% by weight, a gel can be prepared, but the strength of the prepared gel is remarkably low. The gel breaks even with application of a slight force, making handling inconvenient. Therefore, substantially it is preferable to prepare it with a concentration of at least 2% by weight. In the same way, a gel can be prepared even with a concentration of more than 10% by weight, but the viscosity at the time of dispersion of the curdlan becomes extremely high and the subsequent deaeration procedure becomes difficult. Further, the modulus of the gel prepared becomes too high, the ability of close contact with the human body surface is impaired, and thus the gel becomes unsuitable for ultrasonography. For actual diagnosis, a gel prepared with a concentration of not more than 5% by weight is suitable.

The prepared dispersion is sufficiently deaerated under a vacuum and poured gently on to a flat plate or a shaping mold. This is heated at a temperature of at least 60° C., preferably at least 80° C., in a heat sterilization apparatus or hot water bath preferably for at least 10 minutes to cause the gelation. After cooling, a sterilization procedure is followed involving reheating or irradiation to obtain a stronger gel. The longer heating time and the higher heating temperature is, the stronger the gel become.

As the method for preparing the neutralized gel, curdlan powder is dissolved in an aqueous alkaline solution, for example, 1–10% by weight of the curdlan powder in a 5 mM or more, preferably 10–500 mM, aqueous solution of sodium hydroxide. The resultant solution is deaerated under a vacuum, then an equimolar aqueous solution of hydrochloric acid is gently poured in. The resultant solution is allowed to stand for neutralization. At this time, it is possible to easily judge from the outer appearance if the inside has been neutralized by the state of gelation and turbidity accompanying the neutralization. The neutralized curdlan gel thus obtained may be heated at a temperature of at least 60° C., preferably at least 80° C., so as to make the gel stronger.

The above-mentioned methods of preparing a gel may be performed alone or in any combination thereof.

The probe coupling medium of the present invention may contain therein, in addition to the β-1,3 glucans such as curdlan, which are the main component of the gel, one or more substances from among other polymer substances (for example, alginic acid, carrageenan, agar—agar, glucomannan, starch, hyaluronic acid, cellulose, methylcellulose, ethylcellulose, nitrocellulose, and polyvinyl alcohols), various types of salts (for example, sodium salts or potassium salts of phosphoric acid, acetic acid, lactic acid, citric acid, and boric acid and sodium chloride), various types of saccharides (for example, glucose, sucrose, maltose, galactose, mannose, lactose, etc.), urea, glycerin, and silicone, so as to obtain a gel exhibiting more superior characteristics.

The gel thus prepared has a suitable flexibility and is extremely easy to shape and thus is extremely advantageous when thinking of the connection between a probe having a certain shape and a coupling medium. The gel thus prepared displays all excellent acoustic property. That is, the sound velocity is 1497 to 1504 m/s, close to the case of water, and the attenuation rate is 0.06 to 0.16 dB/MHz•cm, the lowest attenuation rate in gels for coupler known today. Further, when the mechanical strength of the gel was measured, it was found that the breaking intensity was $5.37 \times 10^2$ to $4.22 \times 10^3$ g/cm$^2$ and the Young's modulus was $1.96 \times 10^6$ to $6.71 \times 10^6$ dyn/cm$^2$. This shows that the gel has sufficient strength for use as a probe coupling medium.

The probe coupling medium according to the second aspect of the present invention is a gel comprising curdlan or another β-1,3 glucan as the main component and having a water content of at least 80% by weight and is obtained by performing high pressure treatment after gelation by heat. Sometimes, the gel may be reheated for sterilization and improvement of the gel strength.

Next, an example of the manufacturing process will be explained. First, the above-mentioned curdlan-water dispersion is prepared. The concentration of the curdlan is from 1 to 10% by weight, preferably 2 to 5% by weight. The dispersion is deaerated under a vacuum, then gently poured on a plate or in a shaping mold and once again fully deaerated under a vacuum. The result is heated by a heat sterilization apparatus or in a hot water bath to a temperature of at least 60° C., preferably at least 80° C., preferably for at least 10 minutes. After cooling, the resultant gel is subjected to a high pressure treatment of at least 100 kg/cm$^2$, preferably at least 1000 kg/cm$^2$, then is heated at a temperature of at least 60° C., preferably at least 80° C., for preferably at least 10 minutes or is irradiated with radiation for sterilization, whereby the stronger gel is obtained. The longer heating time and the higher heating temperature is, the stronger the gel become.

Recently, a method has been disclosed of increasing the gel strength by subjecting an aqueous dispersion of curdlan to a high pressure treatment, followed by heat treating (see Japanese Unexamined Patent Publication (Kokai) No. 4-158752), but the mechanism thereof is still not clear.

The coupling medium used during centesis and surgery must be sterile in state at the time of use. Toward this end, for the sterilization of the coupling medium, it is desirable to perform the sterilization operation simply in hospitals and to use the most popular heat sterilization apparatus (autoclave).

The powder of the curdlan (for example, curdlan made by Takeda Chemical Industries, Ltd.) being used at the food level contains several kinds of impurities derived from the medium and microorganisms. Also, the powder is slightly brownish. As the starting material for a coupling medium used for centesis or surgery, it is only naturally desirable to use a highly refined starting material which does not include such impurities. However, if such a refined curdlan powder (for example, Curdlan SDS made by Takeda Chemical Industries, Ltd.) is used to prepare a gel by heating, there might be happened cracking and fracturing in the gel along with the increase in temperature (mostly over 100° C.). Note that Curdlan SDS consists of curdlan which has been refined to remove impurities.

The cause for the cracking and fracturing is thought to be the crystallization of curdlan molecules along with heating. To suppress this crystallization, the general practice has been to add other substances. In the case of curdlan, it is difficult to prepare a mixture completely homogeneous on the molecular level since that substance is insoluble in water. Therefore, it has been extremely difficult to avoid cracks and fractures in the refined curdlan gel up to now.

By performing the above-mentioned pressure treatment (100 kg/cm$^2$ or more, preferably 1000 to 10,000 kg/cm$^2$), however, it has become possible to resolve the problem of cracking and fracturing accompanying heating. The method of the pressure treatment may be any one which gives a high pressure of at least 100 kg/cm$^2$. In recent years, Mitsubishi Heavy Industries, Ltd., has marketed an apparatus which can perform high pressure treatment at any temperature. As the procedure for the pressure treatment, rather than the heating and gelation after the pressure treatment of the curdlan dispersion as in Japanese Unexamined Patent Publication (Kokai) No. 4-158752, the method of pressure treatment after heating and gelation at a temperature at which cracking and fracturing do not occur, preferably 60° to 100° C., is preferable and a high resistance to fracturing along with heating can be obtained. The temperature at the time of the pressure treatment does not have to be less than the gelation temperature, since gelation has already occurred, and can be set to any temperature.

The concentration of the curdlan may be any concentration giving a homogeneous dispersion, but 1 to 10% by weight, preferably 2 to 5% by weight, is desirable. When the concentration is less than 1% by weight, the strength of the prepared gel is insufficient, while when more than 10% by weight, the viscosity of the dispersion becomes extremely high and it becomes difficult to obtain a homogeneous gel not including air bubbles. Further, when the gel is used as a coupling medium, a high water content is required to give superior acoustic property and the curdlan concentration is desirably no more than 5% by weight. Even with a concentration of 2 to 5% by weight, the strength of the gel is sufficient and the gel will not break even in procedures pressing it against the body surface and deforming it.

The probe coupling medium of the present invention may contain therein, in addition to β-1,3 glucans such as curdlan, i.e., the main component of the gel, one or more substances from among other polymer substances (for example, alginic acid, carrageenan, agar—agar, glucomannan, starch, hyaronic acid, cellulose, methylcellulose, ethylcellulose, nitrocellulose, and polyvinyl alcohols), various types of salts (for example, sodium salts or potassium salts of phosphoric acid, acetic acid, lactic acid, citric acid, and boric acid and sodium chloride), various types of saccharides (for example, glucose, sucrose, maltose, galactose, mannose, lactose, etc.), urea, glycerin, and silicone, so as to obtain a gel exhibiting more superior characteristics.

The gel thus prepared has a suitable flexibility and is extremely easy to shape and thus is extremely advantageous when thinking of connection between a probe having a certain shape and a coupling medium. The gel thus prepared displays all excellent acoustic property. That is, the sound velocity is 1490 to 1543 m/s, close to the case of water, and the attenuation rate is 0.05 to 0.23 dB/MHz·cm, the lowest attenuation rate in gels for coupler known today. Further, when the mechanical strength of the gel was measured, it was found that the breaking intensity was $5.91 \times 10^2$ to $4.64 \times 10^3$ g/cm$^2$ and the Young's modulus was $2.16 \times 10^6$ to $7.38 \times 10^6$ dyn/cm$^2$. This shows that the gel has sufficient strength for use as a probe intensity medium.

The probe intensity medium according to the third aspect of the present invention is obtained by adding a suitable cross-linking agent to the aqueous alkaline solution of β-1,3 glucan such as curdlan when gelating the curdlan so as to cause cross-linking. For example, 1 to 10% by weight of curdlan powder is added to a 5 mM or more, preferably 25 to 100 mM, aqueous solution of sodium hydroxide, after 0.001 to 2% by weight of a cross-linking agent is added, the resultant solution is sufficiently agitated, and then this is poured into a mold and deaerated. This is allowed to stand at room temperature or is heated at least at 50° C. to cause the cross-linking reaction. After the gelation, the gel is taken out from the mold and neutralized in an equimolar aqueous solution of hydrochloric acid, then is fully washed with water. The heating and washing enable the complete removal of the unreacted cross-linking agent. Further, by heat treatment at least at 60° C., preferably 100 to 121° C., a stronger gelation is possible. The cross-linking agent used here may by any which has at least two functional groups capable of reacting with hydroxyl groups or carboxyl groups per molecule. For example, one or more of a polyhydric glycidylether compound, a polyhydric aziridine compound, a polyhydric amine compound, a polyhydric isocyanate compound, a halomethyl oxirane compound and aldehydes, and divinyl sulfone may be used.

As the polyhydric glycidyl ether compound, there are (poly)ethyleneglycol glycidyl ethers, glycerol polyglycidyl ethers, etc. As the polyhydric aziridine compound, there are 2,2-bishydroxymethylbutanol-tris[3(1-aziridinyl)propionate], 1,6-hexamethylenediethyleneurea, diphenylmethane-bis-4,4'-N,N'-diethyleneurea, etc. As the polyhydric amine compound, there are ethylene diamine, diethylene triamine, triethylene tetramine, tetraethylene pentamine, pentaethylene hexamine, polyethylene imine, etc.

As the polyhydric isocyanate compound, there are 2,4-tolylene diisocyanate, hexamethylene diisocyanate, etc. As the halomethyl oxirane compound, there are epichlorohydrin, epibromohydrin, β-methylepichlorohydrin, β-methylepibromohydrin, etc.

The probe coupling medium of the present invention may contains therein, in addition to the β-1,3 glucan such as curdlan as the main component of the gel, one or more substances from among other polymer substances (for example, alginic acid, carrageenan, agar—agar, glucomannan, starch, hyaluronic acid, cellulose, methylcellulose, ethylcellulose, nitrocellulose, and polyvinyl alcohols), various types of salts (for example, sodium salts or potassium salts of phosphoric acid, acetic acid, lactic acid, citric acid, and boric acid and sodium chloride), various types of saccharides (for example, glucose, sucrose, maltose, galactose, mannose, lactose, etc.), urea, glycerin, and silicone, so as to obtain a gel exhibiting more superior characteristics.

The gel thus prepared has a suitable flexibility and is extremely easy to shape and thus is extremely advantageous when thinking of connection between a probe having a certain shape and a coupling medium. The gel thus prepared displays all excellent acoustic property. That is, the sound velocity is 1499 to 1510 m/s, close to the case of water, and the attenuation rate is 0.07 to 0.20 dB/MHz·cm, the lowest attenuation rate in gels for coupler known today. Further, when the mechanical strength of the gel was measured, it was found that the breaking strength was $1.281 \times 10^3$ to $7.601 \times 10^3$ g/cm$^2$ and the Young's modulus was $2.671 \times 10^6$ to $9.318 \times 10^6$ dyn/cm$^2$. This shows that the gel has sufficient strength for use as a probe coupling medium.

According to the fourth aspect of the present invention, there is provided a coupling medium for a probe of an ultrasonograph comprising a gel composed of β-1,3 glucan and a complex forming compound.

The concentration of the complex forming compound is preferably 5 to 900 mM. As specific examples of the complex forming compound making up part of the probe coupling medium according to the present invention, mention may be made of boric acid, borax, phenylboric acid, sulfonated phenylboric acid, germanic acid, molybdic acid, etc. These may be used alone or any as mixtures of two or more types.

The coupling medium used during centesis and surgery must be sterile in state at the time of use. Toward this end, for the sterilization of the coupling medium, it is desirable to perform the sterilization operation simply in the hospital and to use the most popular type of heat sterilization apparatus (autoclave). However, when a gel of curdlan is heat sterilized, the gel becomes turbid along with the increase in temperature (in most cases over 100° C.). When this is used as the coupling medium for a probe for an ultrasonograph, the resultant ultrasonographic image was hazy and unclear in state.

The above turbidity is considered to be caused by the crystallization of curdlan molecules along with heating. To suppress this crystallization, the general practice has been to add other substances. In the case of curdlan, it is difficult to prepare a mixture completely homogeneous on the molecular level since that substance is insoluble in water. Therefore, it has been extremely difficult to avoid turbidity of the curdlan gel by general additives up to now. However, it became possible in accordance with the present invention to solve the problem of the turbidity of the gel along with heating by adding the above-mentioned complex forming compound.

The concentration of the β-1,3 glucan such as curdlan in accordance with the present invention is not particularly limited so long as it is a concentration by which a homogeneous dispersion may be obtained, but is preferably 1 to 10% by weight, more preferably 2 to 5% by weight. With a concentration of curdlan less than 1% by weight, the strength of the prepared gel sometimes becomes insufficient, while when over 10% by weight, the viscosity of the dispersion becomes high and it becomes difficult to obtain a homogeneous gel not containing air bubbles. Further, when the gel composed of β-1,3 glucan as a main component according to the present invention is used as a coupling medium, a high water content is required to give superior acoustic property and the β-1,3 glucan concentration is desirably not more than 5% by weight. Note that even with a concentration of β-1,3 glucan of 2 to 5% by weight, the strength of the gel is sufficient and the gel will not break even in procedures pressing it against the human body surface and deforming it.

The complex forming compound used in the present invention, as represented by boric acid or boric acid salts, is known to react easily and quickly with saccharides and polyoxy compounds related to the same and to form complex compounds having negative charges (Nature, 161, 96, 1948). As other complex forming compounds, there are known phenylboric acid, sulfonated phenylboric acid, germanic acid, and molybdic acid. The amount of these added is for example preferably 5 to 900 mM (number of millimoles of complex forming compound in one liter of gel), more preferably 30 to 400 mM in range. When the amount added is less than 5 mM, there is a tendency for a lesser effect of improvement of the physical properties and transparency, while conversely when the amount is over 400 mM, not that much greater an effect of improvement can be expected. When the amount is over 900 mM, dissolution becomes difficult. Further, if considering the use of the gel in centesis and surgery, the amount of the complex forming compound added is preferably approximately the isotonic concentration. The transparency of the gel which is prepared depends on the pH of the added boric acid solution. Under weak alkaline conditions, the reaction proceeds, the rate of production of the complex compound becomes higher, and the transparency of the gel is improved as well. However, when considering the use of the coupling medium of the present invention in centesis and surgery, the pH is preferably around 7.4, close to that of blood.

The probe coupling medium of the present invention may contain therein, in addition to the β-1,3 glucan, i.e., the main component, other polymer substances (for example, alginic acid, carrageenan, agar—agar, glucomannan, starch, hyaluronic acid, cellulose, methylcellulose, ethylcellulose, nitrocellulose, and polyvinyl alcohols), various types of salts (for example, sodium salts or potassium salts of phosphoric acid, acetic acid, lactic acid, and citric acid and sodium chloride), various types of saccharides (for example, glucose, sucrose, maltose, galactose, mannose, lactose, etc.), urea, glycerin, and silicone in accordance with need either alone or as mixtures of two or more so as to obtain a gel exhibiting more superior characteristics.

The gel thus prepared has a suitable flexibility and is extremely easy to shape and thus is extremely advantageous when thinking of connection between a probe having a certain shape and a coupling medium. The gel thus prepared displays all excellent acoustic property. That is, the sound velocity is 1499 to 1540 m/s, close to the case of water, and the attenuation rate is 0.06 to 0.20 dB/MHz•cm. Further, when the mechanical strength of the gel was measured, it was found that the breaking intensity was $5.43 \times 10^2$ to $1.32 \times 10^4$ g/cm$^2$ and the Young's modulus was $1.49 \times 10^6$ to $1.57 \times 10^7$ dyn/cm$^2$. This shows that the gel has sufficient strength for use as a probe coupling medium.

EXAMPLES

The present invention will now be explained in further detail by, but is by no means limited to, the following Examples.

Example 1—1

Ninety-seven parts by weight of water were added to 3 parts by weight of curdlan powder (Takeda Chemical Industries, Ltd.) and the mixture was agitated for 10 minutes by a high speed homogenizer (made by Nippon Seiki Co, Ltd., Power Homogenizer, PM-1). The above aqueous curdlan dispersion was sufficiently deaerated under a vacuum, then was poured into a mold and heated at 100° C. for 10 minutes for gelation. This was cooled and taken out from the mold, then was heated at 121° C. for 20 minutes in a heat sterilizer (made by Tomy Seiko; autoclave, SS-245). This operation enabled complete gelation and sterilization simultaneously. The obtained probe coupling medium was 100 mm in length, 50 mm in width, and 15 mm in thickness.

The probe coupling medium thus prepared was measured for its acoustic property, as a result of which values of a sound velocity of 1499 m/s and an attenuation of 0.12 dB/MHz•cm were obtained. Further, a rheometer (made by Fudo Kogyo Co.; NRM-2010J-CW) was used to measure the physical properties, whereupon a breaking intensity of $1.80 \times 10^3$ g/cm$^2$ and Young's modulus of $3.84 \times 10^6$ dyn/cm$^2$ were displayed. Next, the above-mentioned coupling medium was placed between the probe of an ultrasonograph (made by Aloka Co.; SSD-2000) and the skin for image diagnosis, whereupon a clearer sharper image (FIG. 1) was obtained compared with the case of no coupling medium interposed.

Comparative Example 1—1 (See Description of Japanese Examined Patent Publication (Kokoku) No. 62-298342)

Figure 2:
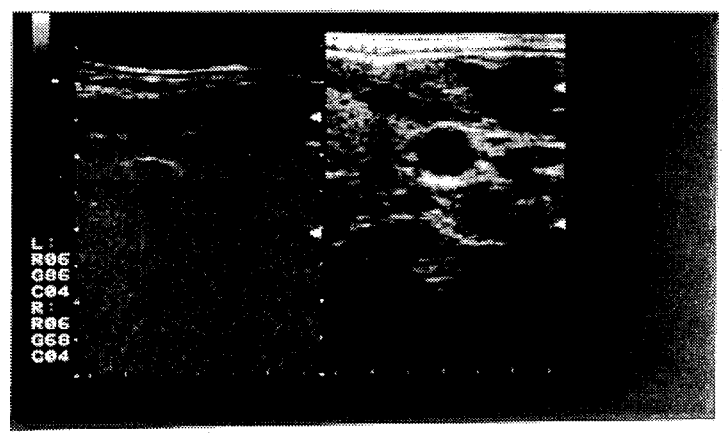
FIG. 2 is a photograph of an ultrasonographic image, in which the right side is the image of a human neck in the case of use of the probe coupling medium prepared in Example 1—1 and the left side is the image in the case of use of the probe coupling medium prepared in Comparative Example 1—1.

A 10% aqueous solution of polyvinyl alcohol with an average degree of polymerization of 1000 and degree of saponification of 87% poured into a flat plate of a thickness of 15 mm and then was frozen at –30° C., followed by thawing. This freezing and thawing operation was repeated 8 times to obtain a gel with a water content of 90%. The gel was measured for the sound velocity and attenuation in accordance with Example 1—1. As a result, the sound velocity was 1500 m/s, about the same as in Example 1—1, but the attenuation rate was 1.0 dB/MHz•cm, about 10 times higher, which is not sufficient for the probe coupling medium of an ultrasonograph. An ultrasonographic image obtained using this coupling medium is shown in FIG. 2.

Comparative Example 1-2 (See Japanese Examined Patent Publication (Kokoku) No. 1-288243)

A 3% aqueous solution of polyvinyl alcohol having an average degree of polymerization of 1500 and a degree of sapurification of 95% was heated at 80° C. to dissolve, placed in a vacuum heating and agitation apparatus for deaeration, allowed to cool to 50° C., cooled to –30° C. to freeze it, then was warmed to room temperature to thaw it. This freezing and thawing operation was repeated 9 times to obtain a gel with a water content of 97%. When the gel was heated and sterilized at 121° C. for 20 minutes in the same way as in Example 1—1, it melted and could not maintain its original shape. As opposed to this, the curdlan gel shown in Example 1—1 showed no deformation due to heating at 121° C. for 20 minutes and showed no change in acoustic property either.

Comparative Example 1-3 (See Japanese Examined Patent Publication (Kokoku) No. 2-21252)

One thousand milliliters of an aqueous solution containing 150 g of acrylamide monomer and 8 g of N,N-methylene bisacrylamide was prepared. To this solution were added 100 ml of a 5% aqueous solution of dimethylaminopropionitrile and 100 ml of 1% potassium persulfate. These were mixed well while taking care not to cause entrainment of air bubbles, then the result was immediately poured into a container of a length of 10 cm, a width of 15 cm, and a depth of 10 cm and caused to react at 40° C. for 10 hours. The gel prepared in this manner contained residual amounts of unreacted acrylamide monomer, whose toxicity is a matter of concern when using the gel for ultrasonography.

Comparative Example 1-4 (See Japanese Unexamined Patent Publication (Kokai) No. 55-63636)

To 100 parts by weight of ordinary temperature water was added 8 parts by weight of a hydrophilic polyurethane having an 80/20 ratio of copolymerization of ethylene oxide and propylene oxide and a 2/4 ratio of —OH of the copolymer and —NCO of the tolylene diisocyanate, which was quickly homogeneously dispersed. The result was immediately poured into a polypropylene container and allowed to stand in that state for 30 minutes to obtain a polyurethane type water containing gel. The gel prepared in the above way contained a residual amount of unreacted ethylene oxide. Ethylene oxide used for gas sterilization as well has in recent years been considered a matter of concern due to the toxicity caused by residual presence. The gel prepared in the above manner therefore has been considered unsuitable as a coupling medium for a probe of an ultrasonograph.

Example 1-2

Probe contact media were prepared by using isotonic aqueous solutions of sodium chloride instead of the water in the above Example and further by adjusting the curdlan concentration from 2 to 5%. By adding salt in this way, it became possible to prevent deterioration of the gel during storage compared with the case of water. Further, no reduction was observed at all in the acoustic property due to the addition of the salt (Table 1—1). Clear ultrasonographic images were obtained by the use of the above probe coupling media.

TABLE 1-1

| Prepared solution | Effects of Salt on Acoustic Property of Curdlan Gel | | |
|---|---|---|---|
| | Curdlan concentration (wt %) | Sound velocity (m/s) | Attenuation rate (dB/MHz · cm) |
| Water | 2 | 1497 | 0.06 |
| | 3 | 1499 | 0.12 |
| | 4 | 1501 | 0.14 |
| | 5 | 1504 | 0.16 |

TABLE 1-1-continued

| Prepared solution | Effects of Salt on Acoustic Property of Curdlan Gel | | |
|---|---|---|---|
| | Curdlan concentration (wt %) | Sound velocity (m/s) | Attenuation rate (dB/MHz · cm) |
| Physiological saline solution | 2 | 1508 | 0.07 |
| | 3 | 1512 | 0.08 |
| | 4 | 1513 | 0.13 |
| | 5 | 1519 | 0.16 |

Example 1-3

Ninety-seven parts by weight of water were added to 2.7 parts by weight of curdlan and 0.3 part by weight of alginic acid and the mixture was agitated at 13,000 rpm for 5 minutes by a high speed homogenizer. The mixture was sufficiently deaerated under a vacuum, then was poured into a mold and heated at 100° C. for 10 minutes for gelation. The gel was cooled and taken out from the mold, then was immersed in a 10% calcium chloride solution for gelation of the alginic acid. After 24 hours, the gel was taken out, washed with water, then heated at 121° C. for 20 minutes in a heat sterilizer to perform complete gelation and sterilization simultaneously. The probe coupling medium thus prepared was used for ultrasonography, whereupon a clearer sharper image was obtained compared with the case of no coupling medium used.

Example 1-4

Three parts by weight of the additives shown in the following table were added to 7 parts by weight amounts of curdlan, then 90 parts by weight of water were added and the results were agitated at 10,000 rpm for 10 minutes in a high speed homogenizer. The results were deaerated under a vacuum, then poured gently on a flat plate and heated at 100° C. for 10 minutes for gelation. The results of observation of the thus prepared gels and the results of the diagnosis of the ultrasonographic images are shown in Table 1-2.

TABLE 1-2

| | Effect of Addition of Additives | |
|---|---|---|
| Additive | Result of observation | Ultrasonographic image |
| Starch | Good | Good |
| Polyvinyl alcohol | Some stickiness on surface | Good |
| Carrageenan | Good | Good |
| Methylcellulose | Some stickiness on surface | Good |
| Scleroglucan | Yellow, good | Good |

Example 1-5

Three parts by weight of curdlan powder were dissolved in 97 parts by weight of a 150 mM sodium hydroxide solution. The resultant mixture was deaerated under a vacuum, then an equal amount of an aqueous solution of 150 mM hydrochloric acid was gently poured in from above. The result was allowed to stand for 48 hours for neutralization. After the neutralization, the gel was taken out and washed with physiological saline solution so as to obtain the probe coupling medium. It became clear that a clear image could be obtained by ultrasonography using this probe coupling medium.

Example 1-6

Ninety-four parts by weight of a physiological saline solution were added to 6 parts by weight of curdlan and the mixture was agitated for 10 minutes by a high speed homogenizer. The resultant mixture and mixture was deaerated under a vacuum, then heated at 100° C. for 10 minutes for gelation. The result was cooled and taken out from the mold, then was placed in a container filled with a physiological saline solution and irradiated with gamma rays for sterilization. The physical properties of the obtained probe coupling medium were a breaking strength of $5.23 \times 10^3$ $g/cm^2$ and a Young's modulus of $7.23 \times 10^6$ $dyn/cm^2$. The probe coupling medium was used for ultrasonography, whereupon a clearer sharper image was obtained compared with the case of no coupling medium interposed.

Example 1-7

Ninety-seven parts by weight of urea solutions of the concentrations shown in the following table were added to 3 parts by weight of curdlan powder and the mixtures were agitated for 10 minutes by a high speed homogenizer. The above aqueous curdlan dispersions were sufficiently deaerated under a vacuum, then were poured into molds and heated at 100° C. for 10 minutes for gelation. These were cooled and taken out from the molds, then were heated at 121° C. for 20 minutes in a heat sterilizer. This operation enabled complete gelation and sterilization simultaneously. The breaking intensity and Young's modulus are shown in Table 1-3. The above-mentioned coupling media were placed between the probe of an ultrasonograph and the skin for image diagnosis, whereupon clearer sharper images were obtained compared with the case of no contact media interposed.

TABLE 1-3

Effect of Addition of Urea

| Urea concentration (mM) | Breaking intensity ($\times 10^3$ $g/cm^2$) | Young's modulus ($\times 10^6$ $dyn/cm^2$) |
| --- | --- | --- |
| 10 | 1.70 | 4.44 |
| 50 | 2.49 | 4.97 |
| 100 | 2.98 | 4.20 |
| 500 | 1.50 | 1.99 |

Example 1-8

Ninety-six point five part by weight amounts of glucose and sucrose aqueous solutions shown in the following Table were added to 3.5 parts by weight of curdlan powder and the mixtures were agitated for 10 minutes by a high speed homogenizer. The above curdlan dispersions were sufficiently deaerated under a vacuum, then were poured into molds and heated at 100° C. for 10 minutes for gelation. These were cooled and taken out from the molds, then were heated at 121° C. for 20 minutes in a heat sterilizer. This operation enabled complete gelation and sterilization simultaneously. The breaking intensity and Young's modulus are shown in Table 1-4. The above-mentioned contact media were placed between the probe of an ultrasonograph and the skin for image diagnosis, whereupon clearer sharper images were obtained compared with the case of no contact media interposed.

TABLE 1-4

Effect of Addition of Saccharide

| Aqueous saccharide solution (concentration; mM) | Breaking intensity ($\times 10^3$ $g/cm^2$) | Young's modulus ($\times 10^6$ $g/cm^2$) |
| --- | --- | --- |
| Glucose (75) | 3.41 | 7.10 |
| Glucose (150) | 3.12 | 6.51 |
| Sucrose (75) | 2.24 | 5.48 |
| Sucrose (150) | 2.68 | 5.52 |

Example 1-9

Ninety-six point five parts by weight of an 150 mM aqueous solution of sodium lactate were added to 3.5 parts by weight of curdlan and the mixture was agitated for 10 minutes by a high speed homogenizer. The above aqueous curdlan dispersion was sufficiently deaerated under a vacuum, then was poured into a mold and heated at 100° C. for 10 minutes for gelation. This was cooled and taken out from the mold, then was heated at 121° C. for 20 minutes in a heat sterilizer. This operation enabled complete gelation and sterilization simultaneously. The coupling medium was placed between the probe of an ultrasonograph and the skin for image diagnosis, whereupon a clearer sharper image was obtained compared with the case of no coupling medium interposed.

Example 1-10

Ten grams of scleroglucan (made by San-Ei Gen F.F.I. Inc.) were dissolved in 10 liters of 0.03M $NaIO_4$ and the resultant mixture was allowed to stand at 5° C. for five days. Next, 500 ml of ethylene glycol was added and the mixture agitated, then dialysis was performed at 5° C. for two days. Ammonia water was added to the dialyzed solution to make it weakly alkaline, then 5 g of $NaBH_4$ were added and the mixture was allowed to stand. Next, this was neutralized by 1N acetic acid, then once again dialyzed against flowing water at 5° C. and evaporated to dryness. The powder thus prepared was digested by β-1,3 glucanase, then the decomposed product solution was spotted on No. 50 filter paper (made by Toyo Roshi Kaisha, Ltd.) and developed by n-butanol/isopropanol/water=3:12:4, whereupon it became clear that the product was curdlan-like β-1,3 glucan with about 95% of the β-1,6 bond side chains removed.

Ninety-two parts by weight of physiological saline solution were added to 8 parts by weight of this product and the mixture was agitated for 10 minutes by a high speed homogenizer (made by Nippon Seiki Co.; Power Homogenizer, PM-1). The mixture was sufficiently deaerated under a vacuum, then was poured into a mold and heated at 80° C. for 10 minutes for gelation. This was cooled and taken out from the mold, then was heated at 121° C. for 20 minutes in a heat sterilizer (made by Tomy Seiko, autoclave, SS-245), whereby complete gelation and sterilization were performed.

The coupling medium thus prepared was measured for its acoustic property, as a result of which values of a sound velocity of 1510 m/s and an attenuation rate of 0.19 dB/MHz•cm were obtained. Further, a rheometer (made by Fudo Kogyo Co.; NRM-2010J-CW) was used to measure the physical properties, whereupon a breaking intensity of $4.50 \times 10^3$ $g/cm^2$ and Young's modulus of $7.84 \times 10^6$ $dyn/cm^2$ were displayed.

The obtained probe coupling medium was used for ultrasonography, whereupon a clearer sharper image was obtained compared with the case of no coupling medium used.

Example 1-11

One gram of Schizophyllan (Gakken Seiyaku K.K.) was used and the same procedure followed on a scale of 1/10th that of the above Example 1-10 to cut the branch side chains. Thus, it becomes clear that the product was curdlan-like β-1,3 glucan with about 93% of the β-1,6 bond side chains removed.

Ninety-five parts by weight of a physiological saline solution were added to 5 parts by weight of this product and the mixture was agitated for 10 minutes by a high speed homogenizer. The mixture was sufficiently deaerated under a vacuum, then was poured into a mold and heated at 100° C. for 20 minutes for gelation. This was cooled and taken out from the mold, then was heated at 121° C. for 20 minutes in a heat sterilizer, whereby complete gelation and sterilization were performed.

The coupling medium thus prepared was measured for its acoustic property, as a result of which values of a sound velocity of 1501 m/s and an attenuation rate of 0.15 dB/MHz·cm were obtained. Further, a rheometer was used to measure the physical properties, whereupon a breaking intensity of $3.20 \times 10^3$ g/cm$^2$ and Young's modulus of $5.56 \times 10^6$ dyn/cm$^2$ were displayed. The probe coupling medium thus obtained was used for ultrasonography, whereupon a clearer sharper image was obtained compared with the case of no coupling medium used.

Example 2-1—1

Ninety-six point five parts by weight of water were added to 3.5 parts by weight of Curdlan SDS (made by Takeda Chemical Industries, Ltd.) and the mixture was agitated for 10 minutes by a high speed homogenizer. The above aqueous curdlan dispersion was sufficiently deaerated under a vacuum, then was poured into a mold and heated at 100° C. for 10 minutes for gelation. This was cooled and taken out from the mold, then was packed into a heat seal pack and treated at 21° C. and 3000 kg/cm$^2$ for 10 minutes in a high pressure treatment apparatus. Then, this was heated at 121° C. for 20 minutes in a heat sterilizer. This operation enabled complete gelation and sterilization simultaneously.

The probe coupling medium thus prepared was measured for its acoustic property, as a result of which values of a sound velocity of 1502 m/s and an attenuation of 0.14 dB/MHz·cm were obtained. Further, a rheometer (made by Fudo Kogyo Co.; NRM-2010J-CW) was used to measure the physical properties, whereupon a breaking strength of $2.97 \times 10^3$ g/cm$^2$ and Young's modulus of $5.19 \times 10^6$ dyn/cm$^2$ were displayed. Next, the above-mentioned probe coupling medium was placed between the probe of an ultrasonograph and the skin for image diagnosis, whereupon a clearer sharper image was obtained compared with the case of no coupling medium interposed.

Example 2-1-2

Exactly the same procedure was followed as in Example 2-1—1 to obtain a curdlan gel except for the high pressure treatment. When heated at 121° C. for 20 minutes, three out of 10 samples of the gel showed cracks and fractures and therefore the heat resistance was insufficient for a coupling medium of a probe of an ultrasonograph. As opposed to this, not even one sample out of 10 of the high pressure treated gel of Example 2-1—1 showed any cracks or fractures even when repeated treated at 121° C. for 20 minutes, so the heat resistance was clearly improved.

Example 2-1-3

A 3.5% curdlan dispersion was prepared and deaerated in accordance with Example 2-1—1. The dispersion was packed into a heat seal pack and treated at 21° C., 3000 kg/cm$^2$, and 10 minutes by a high pressure treatment apparatus. Then, the treated dispersion was gently poured into a mold and heated at 100° C. for 10 minutes for gelation. This was cooled, then taken out from the mold. Next, the gel was sterilized by heating at 121° C. for 20 minutes, whereupon two out of 10 samples showed cracks and fractures. Therefore, the heat resistance was not sufficient for a coupling medium for a probe of an ultrasonograph.

Example 2—2

Probe coupling media were prepared by using isotonic aqueous solutions of sodium chloride instead of the water in the above example and further by adjusting the curdlan concentration from 2 to 5%. By adding salt in this way, it became possible to prevent deterioration of the gel during storage compared with the case of water. Further, no reduction was observed at all in the acoustic property due to the addition of the salt (Table 2-1). Clear ultrasonographic images were obtained by the use of the above probe coupling mediums.

TABLE 2-1

Effects of Salt on Acoustic Property of Curdlan Gel

| Prepared solution | Curdlan concentration (wt %) | Sound velocity (m/s) | Attenuation rate (dB/MHz · cm) |
|---|---|---|---|
| Water | 2 | 1495 | 0.07 |
|  | 3 | 1498 | 0.09 |
|  | 4 | 1508 | 0.13 |
|  | 5 | 1507 | 0.16 |
| Physiological saline solution | 2 | 1510 | 0.08 |
|  | 3 | 1515 | 0.09 |
|  | 4 | 1519 | 0.14 |
|  | 5 | 1522 | 0.17 |

Example 2-3

Ninety-two point seven parts by weight of water were added to 7 parts by weight of Curdlan SDS and 0.3 part by weight of alginic acid and the mixture was agitated at 13,000 rpm for 5 minutes by a high speed homogenizer. This was sufficiently deaerated under a vacuum, then was poured into a mold and heated at 100° C. for 10 minutes for gelation. The gel was cooled and taken out from the mold, then was immersed in a 10 percent calcium chloride solution for gelation of the alginic acid. After 24 hours, the gel was taken out, washed with water, then packed into a heat seal pack and treated at 21° C. and 5000 kg/cm$^2$ for 10 minutes in a high pressure treatment apparatus. Then, this was heated at 121° C. for 20 minutes in a heat sterilizer. This operation enabled complete gelation and sterilization simultaneously. The probe coupling medium thus prepared was used for ultrasonography, whereupon a clearer sharper image was obtained compared with the case of no coupling medium used.

Example 3-1

Three point five parts by weight of curdlan (Takeda Chemical Industries, Ltd.) were dissolved in 96.25 parts by weight of a 25 mM sodium hydroxide solution, then 0.25 part by weight of ethylene glycol diglycidyl ether (Denacol EX-810P Medical Grade; Nagase Chemicals Ltd.) was added and the mixture was sufficiently agitated. This was sufficiently deaerated under a vacuum, then was gently poured into a mold and was once again deaerated under a vacuum. The result was then heated at 121° C. for 20 minutes for gelation. The gel was cooled, then immersed in an equimolar amount of a hydrochloric acid solution and neutralized with shaking for 24 hours. After the neutralization, the external solution was replaced with a physiological saline solution and the result was washed for 24 hours with shaking once again. The thus obtained gel was sealed in a suitable heat seal pack and was heated at 121° C. for 20 minutes for sterilization.

The gel thus prepared was measured for its acoustic property, as a result of which values of a sound velocity of 1503 m/s and an attenuation rate of 0.13 dB/MHz·cm were obtained. Further, it was measured for its physical properties by a rheometer (made by Fudo Kogyo Co.; NRM-2010 J-CW), whereupon the physical properties of the thus prepared cross-linked curdlan gel were found to be a breaking intensity of $3.852 \times 10^3$ g/cm and a Young's modulus of $5.067 \times 10^6$ dyn/cm$^2$. Compared with uncrosslinked curdlan gel, the Young's modulus was about the same, but the breaking intensity was improved.

In ultrasonographic image using the above cross-linked curdlan gel, a clearer sharper image was obtained compared with the case of no use of the gel.

Further, the above-mentioned cross-linked curdlan gel was immersed in a physiological saline solution, stored at 5° C., 25° C., and 50° C., and evaluated as to its stability, whereupon no visible changes could be observed even after three months.

Example 3-2

Five parts by weight of curdlan were dissolved in 94 parts by weight of a 25 mM sodium hydroxide solution, then 1 part by weight of divinyl sulfone was added, the mixture was agitated, then the mixture was heated at 100° C. for 10 minutes. The semigelatinous substance obtained by the above procedure was homogenized while adding an equimolar amount of a 1N hydrochloric acid solution. The homogenized sol was poured on a plate of a thickness of 10 mm and was frozen at –20° C. for 12 hours, was freeze-dried for 48 hours, then was pulverized to obtain the cross-linked curdlan powder.

Ninety-two parts by weight of water were added to 1 part by weight of the cross-linked curdlan powder and 7 part by weight of curdlan powder and the mixture was agitated at 13,000 rpm for 10 minutes by a high speed homogenizer to obtain a homogeneous dispersion. This was sufficiently deaerated under a vacuum, then was gently poured into a mold and once again deaerated under a vacuum, then was heated at 100° C. for 10 minutes for gelation. This was cooled and taken out from the mold, then was heated at 121° C. for 20 minutes to perform complete gelation and sterilization simultaneously.

In ultrasonographic image using the above gel, a clearer sharper image was obtained compared with the case of no use.

Example 3—3

Exactly the same procedure was followed as in Example 3-2 to obtain a cross-linked curdlan powder except that the cross-linking agent was changed to epichlorohydrin. Ninety-six point five parts by weight of water were added to 3.5 parts by weight of the cross-linked curdlan powder and the mixture was agitated for 10 minutes by a high speed homogenizer. This was sufficiently deaerated under a vacuum, then was poured into a mold and heated at 100° C. for 10 minutes for gelation. This was cooled and taken out from the mold, then was taken out and heated at 121° C. for 20 minutes in a heat sterilizer. This procedure enabled complete gelation and sterilization.

In ultrasonography using the above gel, a clearer sharper image was obtained compared with the case of no use of the gel.

Example 3-4

A 96.998 part by weight amount of 50 mM NaOH solution was added to 2.7 parts by weight of curdlan and 0.3 part by weight of alginic acid and the mixture was agitated at 13,000 rpm for 5 minutes in a high speed homogenizer. The agitation was then stopped, 0.002 part by weight of divinyl sulfone was added, then agitation was performed once again at 6,000 rpm for 5 minutes. The result was deaerated under a vacuum, then was poured into a mold and heated at 121° C. for 10 minutes for gelation. The gel was cooled and taken out of the mold, then was immersed in a 10% calcium chloride solution for gelation of the alginic acid. At this time, 0.1N HCl was added dropwise at suitable times to adjust the pH of the calcium chloride solution to 6 to 7. After 24 hours, the gel was taken out and washed with water, then was immersed in a physiological saline solution for 48 hours. Next, a heat sterilizer was used to heat the gel at 121° C. for 20 minutes to sterilize it.

The thus prepared probe coupling medium was used for ultrasonography, whereupon a clearer sharper image was obtained compared with the case of no coupling medium used.

Example 4-1—1

Figure 3:
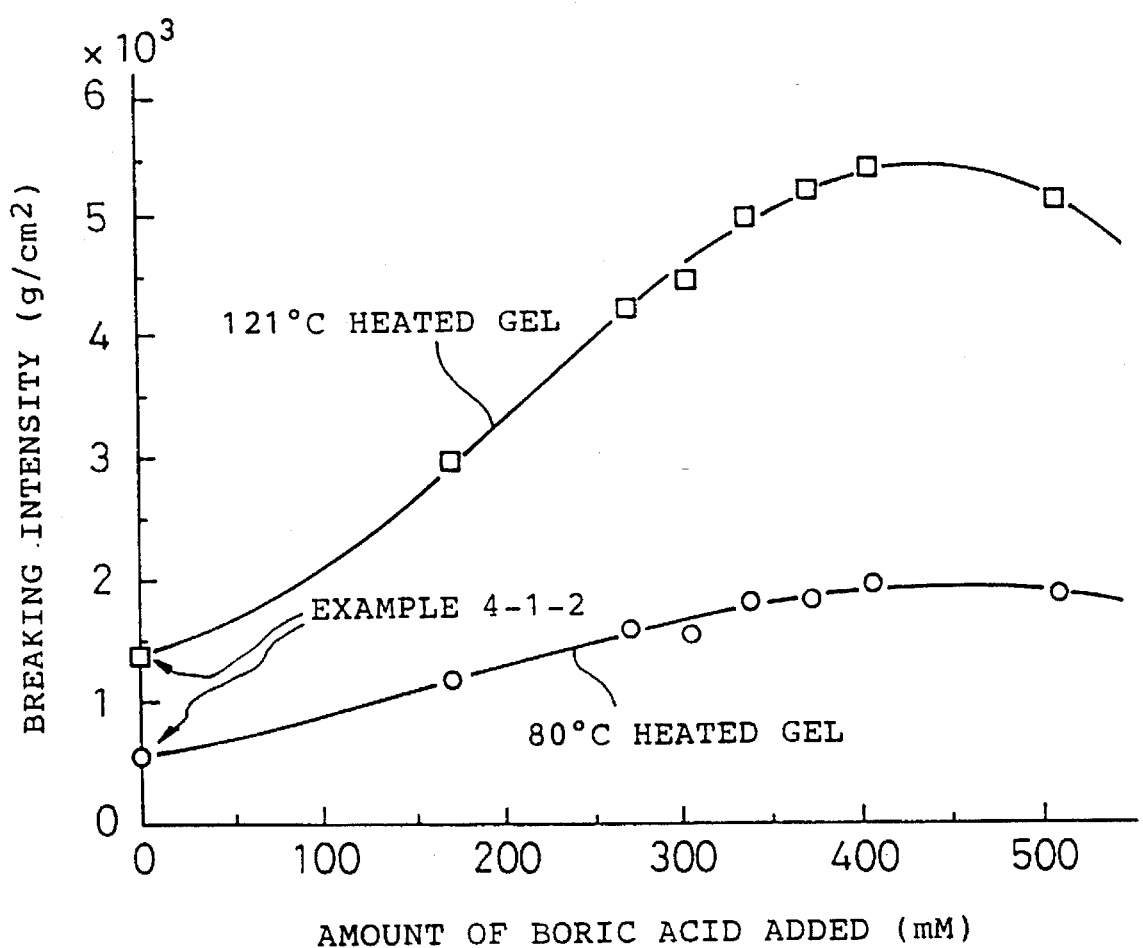
FIG. 3 is a graph showing the change in the breaking intensity of the gel caused by the addition of boric acid in Examples 4-1—1 and 4-1-2, obtained by dicing the curdlan gel prepared in accordance with Example 4-1—1 (gel was prepared by heating at 80° C. and 121° C. for sterilization) into 20 ×20 ×10 mm pieces and using a rheometer to measure the breaking intensity (the points shown are the average values for three measurements of the same samples).
Figure 4:
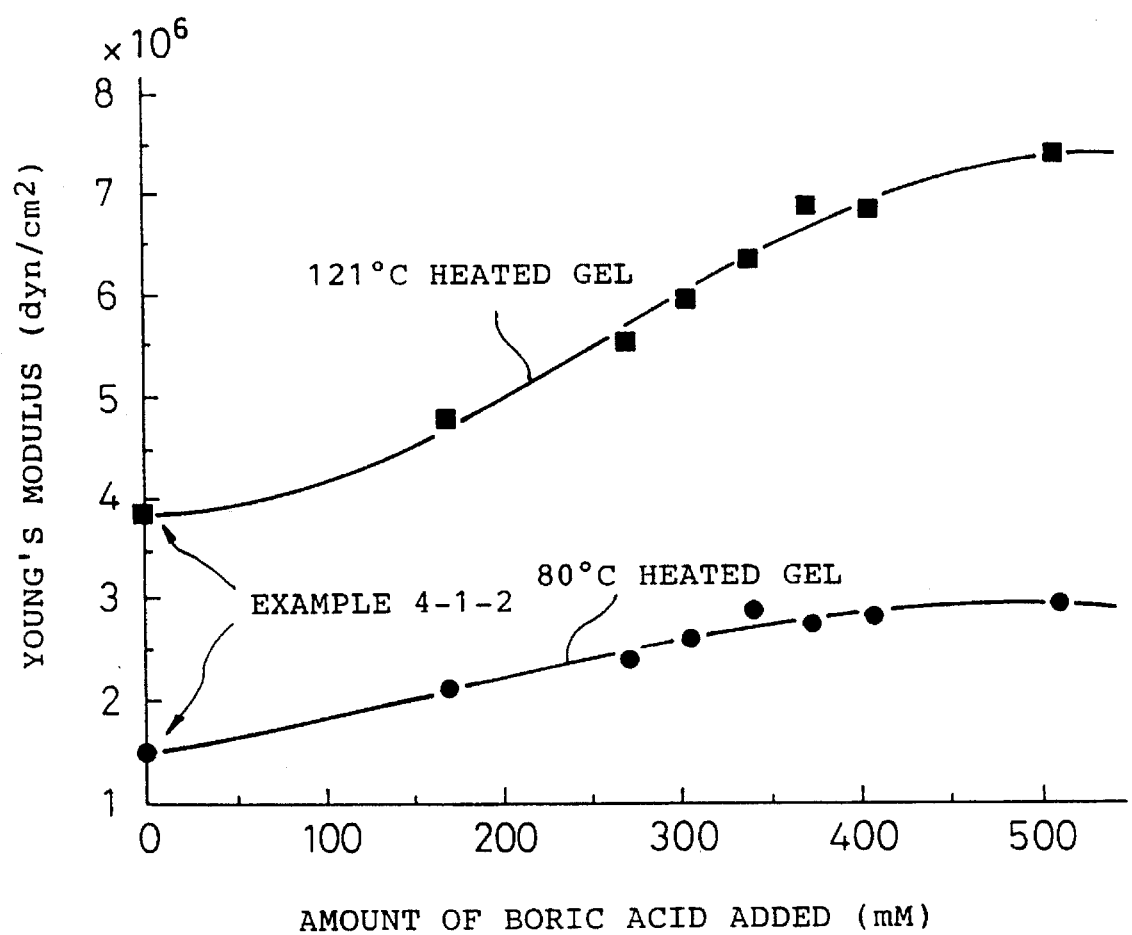
FIG. 4 is a graph showing the change in the Young's modulus of the gel caused by the addition of boric acid in Examples 4-1—1 and 4-1-2, obtained by dicing the curdlan gel prepared in accordance with Example 4-1—1 (gel was prepared by heating at 80° C. and 121° C. for sterilization) into 20 ×20 ×10 mm pieces and using a rheometer to measure the Young's modulus (the points shown are the average values for three measurements of the same samples).
Figure 5:
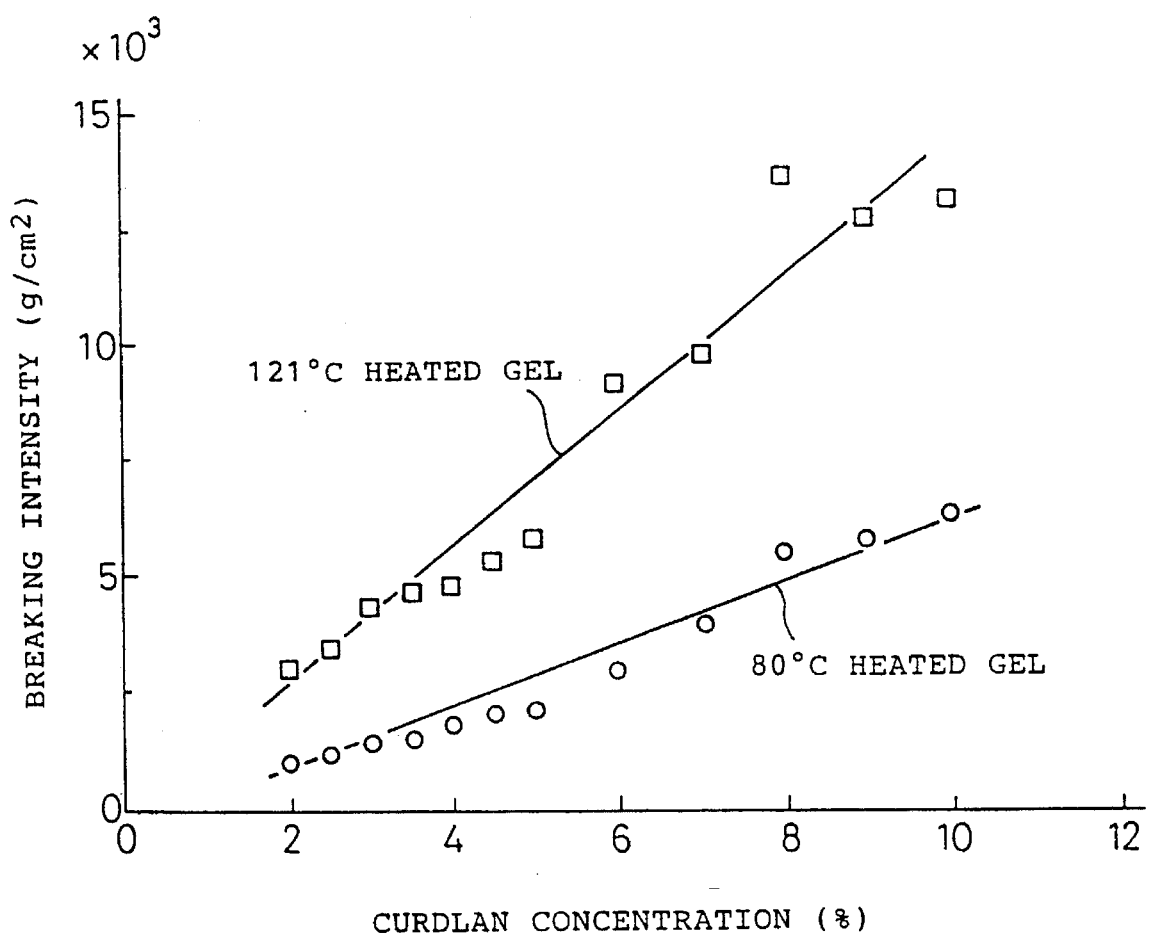
FIG. 5 is a graph showing the relationship between the curdlan concentration and the breaking intensity of the gel caused in Example 4-2, obtained by dicing the curdlan gel prepared in accordance with Example 4-2 (gel was prepared by heating at 80° C. and 121° C. for sterilization) into 20 ×20 ×10 mm pieces and using a rheometer to measure the breaking intensity (the points shown are the average values for three measurements of the same samples).
Figure 6:
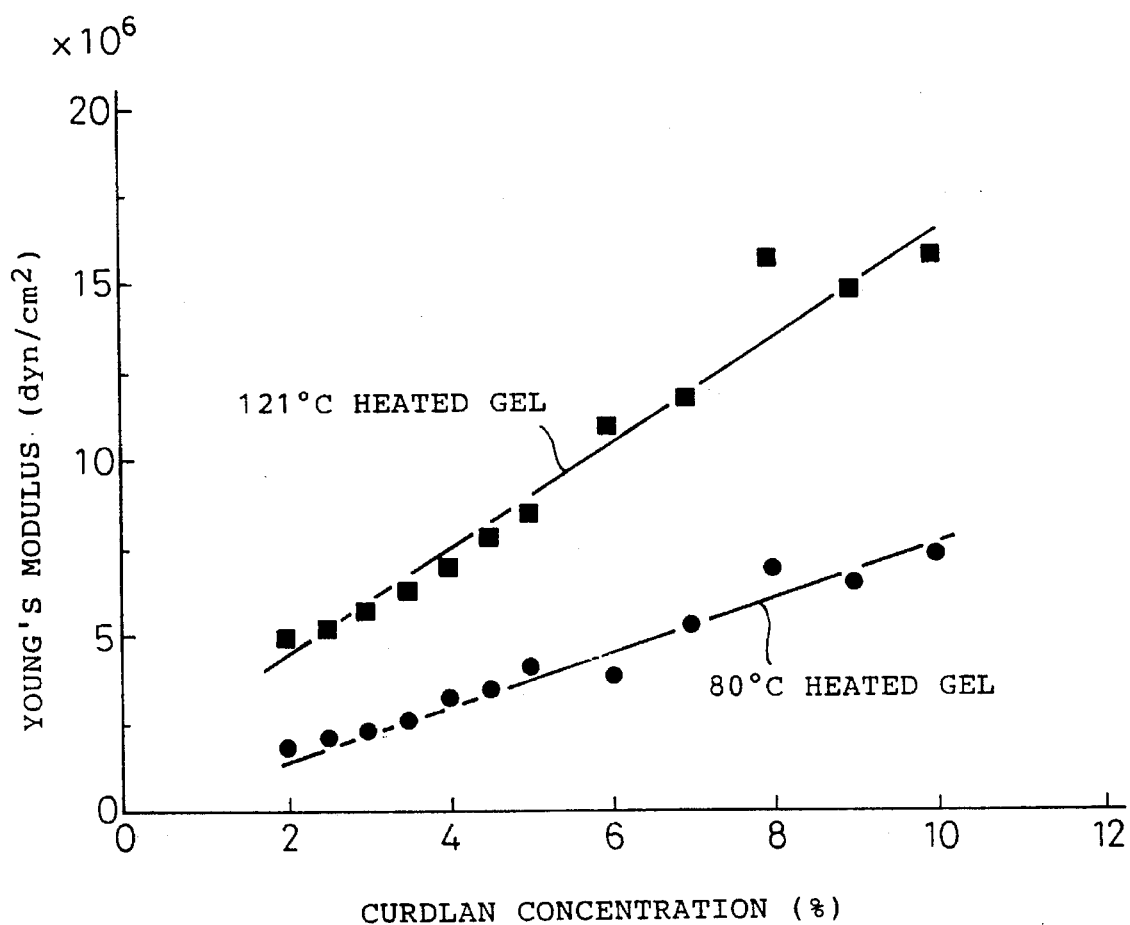
FIG. 6 is a graph showing the relationship between the curdlan concentration and the Young's modulus of the gel caused in Example 4-2, obtained by dicing the curdlan gel prepared in accordance with Example 4-2 (gel was prepared by heating at 80° C. and 121° C. for sterilization) into 20 ×20 ×10 mm pieces and using a rheometer to measure the Young's modulus (the points shown are the average values for three measurements of the same samples).

Ninety-six point five parts by weight of 170 to 510 mM boric acid solutions (pH 7.4) were added to 3.5 parts by weight of curdlan powder (made by Takeda Industries Co., Ltd.) and the mixtures were agitated for 10 minutes at 13,000 rmp by a high speed homogenizer (made by Nippon Seiki Co., Power Homogenizer, PM-1) to obtain homogeneous dispersions. These were sufficiently deaerated under a vacuum, then were gently poured into molds, were once again deaerated under a vacuum, and then were heated at 80° C. for 20 minutes for gelation. The thus obtained gels were sealed in suitable heat seal packs and were heated at 121° C. for 20 minutes in a heat sterilizer (made by Tomy Seiko; autoclave, SS-245) for sterilization. The thus prepared gels were measured for their breaking strengths and Young's modulus using a rheometer (made by Fudo Kogyo Co.; NRM-2010J-CW). The results are shown in FIG. 3 and FIG. 4.

A look at the physical properties of the thus prepared boric acid-added curdlan gels shows a trend of a rise in the breaking intensity and Young's modulus along with an increase in the amount of boric acid added, but the breaking intensity became maximum near 400 mM. With any further addition, the strength conversely fell. Further, to evaluate the transparency, the curdlan gels prepared above were diced to 20×20×1 mm and the absorbances at 660 nm and transmittance were measured by a spectrophotometer (made by Japan Spectroscopic Co., Ltd.: V-550). The results are shown in Table 4-1.

TABLE 4-1

Evaluation of Transparency (Effect of Addition of Boric Acid)

| Boric acid (mM) | ABS$_{660}$ | T % |
| --- | --- | --- |
| 510 | 0.046 | 89.9 |
| 408 | 0.031 | 93.0 |
| 374 | 0.034 | 92.6 |
| 340 | 0.030 | 93.3 |
| 306 | 0.031 | 93.0 |
| 272 | 0.030 | 93.3 |
| 170 | 0.064 | 86.4 |
| 0 (Comp. Example) | 0.288 | 51.6 |

From the results of Table 4-1, it is learned that the transparency is improved by addition of boric acid to curdlan. Further, the absorbance value became extremely small in the range of the addition of 272 to 408 mM of boric acid. With any further addition, the transparency dropped.

In ultrasonographic image using the above boric acid-added curdlan gel, a clearer sharper image was obtained compared with the case of no use of the gel.

That is, a high correlation was observed between the transparency of the gel and the ultrasonographic image and it was confirmed that a sharp image can be obtained in ultrasonography using the transparent gel according to the present invention.

Example 4-1-2

Ninety-six point five parts by weight of water were added to 3.5 parts by weight of curdlan powder and the mixture was agitated in a high speed homogenizer for 10 minutes. The curdlan-water dispersion obtained was fully deaerated under a vacuum, then poured into a mold and heated at 80° C. for 20 minutes to cause gelation. Next, the gel was cooled and taken out from the mold, then heated at 121° C. for 20 minutes in a heat sterilizer to cause complete gelation and sterilization.

The thus prepared gel was measured for its physical properties and transparency in the same way as in Example 4-1—1. The results are shown in FIG. 3, FIG. 4, and Table 4-1. In ultrasonographic image diagnosis using this, the picture was little hazy and somewhat unclear.

Example 4-2

Two to 10 parts by weight of curdlan were added to 340 mM boric acid solutions (adjusted to pH of 7.4 by NaOH) and the same procedure was followed as in Example 4-1—1 to agitate the mixtures by a high speed homogenizer and obtain homogeneous dispersions. These were deaerated under a vacuum, then poured into molds and again deaerated under a vacuum, then were heated at 80° C. for 10 minutes to cause gelation. After cooling, the results were taken out from the molds and heated at 121° C. for 20 minutes to cause complete gelation and sterilization simultaneously. The gels were allowed to cool at room temperature, then were diced to 20×20×1 mm. The absorbances at 660 nm and the transmittances were measured using a spectrophotometer (made by Japan Spectroscopic Co., Ltd., V-550).

TABLE 4-2

Evaluation of Transparency (Effect of Concentration of Curdlan)

| Curdlan concentration (wt %) | ABS$_{660}$ | T % |
| --- | --- | --- |
| 2 | 0.092 | 81.0 |
| 2.5 | 0.061 | 86.9 |
| 3 | 0.042 | 90.8 |
| 3.5 | 0.029 | 93.6 |
| 4 | 0.029 | 93.6 |
| 4.5 | 0.022 | 95.1 |
| 5 | 0.014 | 97.0 |
| 6 | 0.028 | 93.7 |
| 7 | 0.032 | 93.0 |
| 8 | 0.034 | 92.5 |
| 9 | 0.033 | 92.6 |
| 10 | 0.043 | 90.5 |

It became clear that as the amount of addition of curdlan increased, the gels became stronger and harder. Further, the transparency was improved the most with a curdlan concentration of 5% by weight. In ultrasonography using the above gels, clearer, sharper images could be obtained compared with the case of no use.

Example 4-3

Figure 7:
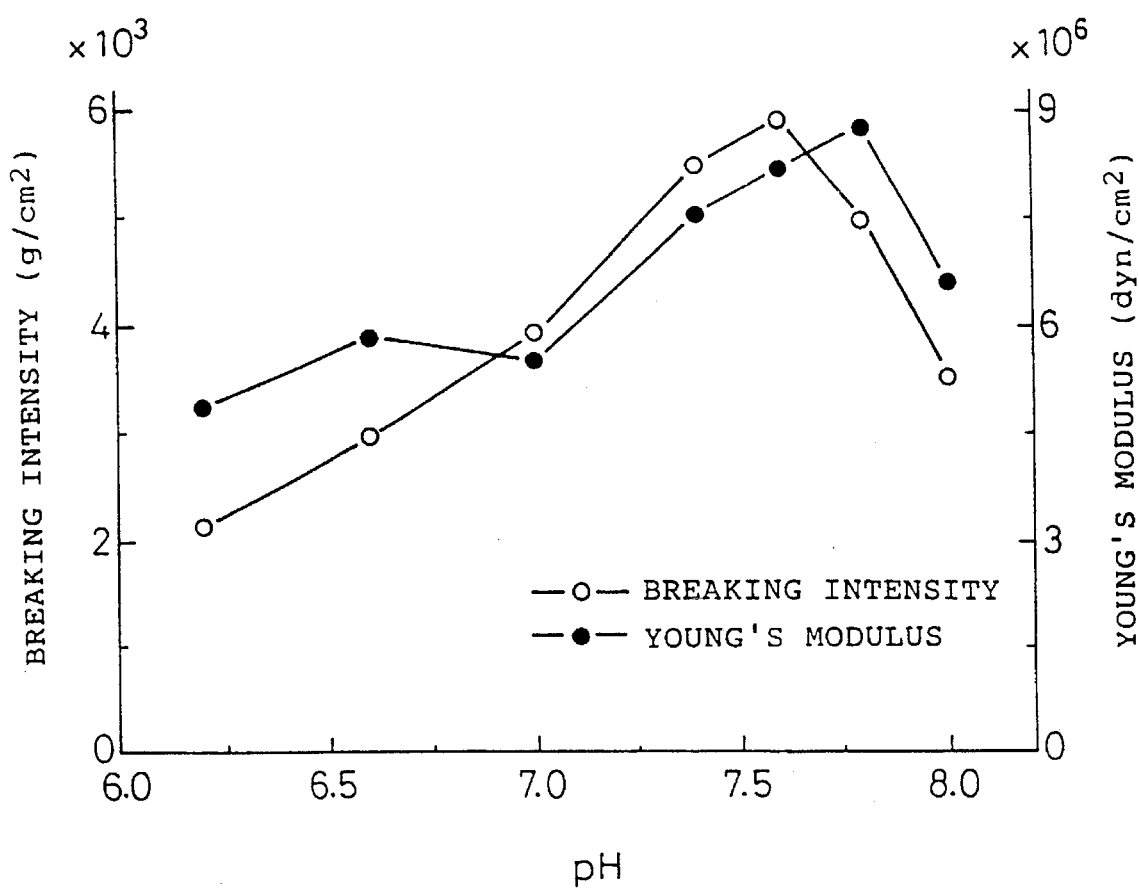
FIG. 7 is a graph showing the effects of the pH on the physical properties (breaking intensity, Young's modulus) of the curdlan gel in Example 4-3, obtained by dicing the curdlan gel prepared in accordance with Example 4-3 (gel was prepared by heating at 121° C. for sterilization) into 20 ×20 ×10 mm pieces and using a rheometer to measure the breaking intensity and the Young's modulus (the points shown are the average values for three measurements of the same samples).

Portions of boric acid solutions of varying pH's (6.2, 6.6, 7.0, 7.4, 7.6, 7.8, 8.0) were added to 3.5 part by weight amounts of curdlan to give isotonic concentrations and the same procedure was followed as in Example 4-1-1 to obtain boric acid-added curdlan gels at different pH's. These were heated and sterilized at 121° C. for 20 minutes, then the physical properties were measured. The results are shown in FIG. 7. Further, the transparencies of the gels were found by allowing the heat sterilized gels to cool at room temperature, dicing them to 20×20×1 mm, and measuring the absorbances at 660 nm and transmittances by a spectrophotometer (made by Japan Spectroscopic Co., Ltd., V-550). The results are shown in Table 4-3. As clear from these results, the breaking intensity was highest at a pH of 7.6 and the Young's modulus at a pH of 7.8. Further, the transparency was most improved at a pH of 7.4.

TABLE 4-3

Evaluation of Transparency (Effect of pH)

| pH | ABS$_{660}$ | T % |
| --- | --- | --- |
| 6.2 | 0.142 | 72.0 |
| 6.6 | 0.070 | 85.2 |
| 7.0 | 0.042 | 90.8 |
| 7.4 | 0.022 | 95.0 |
| 7.6 | 0.026 | 94.2 |
| 7.8 | 0.096 | 80.3 |
| 8.0 | 0.174 | 67.0 |

Example 4—4

Ninety-two parts by weight of a 750 mM phenylboric acid solution was added to 8 parts by weight of curdlan and the mixture was agitated for 10 minutes by a high speed homogenizer. The result amt mixture was deaerated under vacuum, then poured into a mold and heated at 70° C. for 30 minutes for gelation. The result was cooled and taken out from the mold, then was heated at 121° C. for 20 minutes in a heat sterilizer. This operation enabled more complete gelation and sterilization. In ultrasonography using the obtained gel, a clearer sharper image was obtained compared with the case of no coupling medium used.

Example 4-5

Ninety-seven parts by weight of a 300 mM boric acid solution (adjusted to pH of 7.6 by NaOH) was added to 2.7 parts by weight of curdlan and 0.3 part by weight of alginic acid and the mixture was agitated at 13,000 rpm for 5 minutes by a high speed homogenizer. The result was deaerated under a vacuum, then poured into a mold and heated at 80° C. for 10 minutes for gelation. The result was cooled and taken out from the mold, then was immersed in a 10 percent calcium chloride solution for 24 hours to cause gelation of the alginic acid. Next, a heat sterilizer was used for heating and sterilization at 121° C. for 20 minutes. The resultant probe coupling medium was used for ultrasonography, whereupon a clearer sharper image was obtained compared with the case of no coupling medium used.

Example 4-6

Ninety-seven point five parts by weight of a 500 mM boric acid solution (adjusted to pH of 7.2 by NaOH) was added to 2 parts by weight of curdlan and 0.5 part by weight of lentinan (made by Ajinomoto Co.) and the mixture was agitated at 13,000 rpm for 5 minutes by a high speed homogenizer. The result was deaerated under a vacuum, then poured into a mold and heated at 100° C. for 10 minutes for gelation. Next, a heat sterilizer was used for sterilization at 121° C. for 20 minutes. The resultant probe coupling medium was used for ultrasonography, whereupon a clearer sharper image was obtained compared with the case of no coupling medium used.

Example 4-7

Ten grams of scleroglucan (made by San-Ei Gen F.F.I, Inc.) were dissolved in 10 liters of 0.03M NaIO$_4$ and the result was allowed to stand at 5° C. for five days. Next, 500 ml of ethylene glycol were added and the mixture agitated, then dialysis was performed at 5° C. for two days. Ammonia water was added to the dialyzed solution to make it weakly alkaline, then 5 g of NaBH$_4$ were added and the mixture was allowed to stand. Next, this was neutralized by 1N acetic acid, then once again dialyzed against flowing water at 5° C. and evaporated to dryness. The thus prepared powder was digested by β-1,3 glucanase, then the decomposed product solution was spotted on No. 50 filter paper (made by Toyo Roshi Kaisha Ltd.) and developed by n-butanol/iso-propanol/water =3:12:4, whereupon it became clear that the product was curdlan-like β-1,3 glucan with about 95% of the β-1,6 bond side chains removed. Ninety-two parts by weight of 340 mM boric acid solution (pH 7.4) were added to 8 parts by weight of this product and the mixture was agitated for 10 minutes by a high speed homogenizer. The mixture was sufficiently deaerated under a vacuum, then was poured into a mold and heated at 80° C. for 20 minutes for gelation. The gel was cooled and taken out from the mold, then was heated at 121° C. for 20 minutes in a heat sterilizer, whereby complete gelation and sterilization were performed. The probe coupling medium obtained was used for ultrasonography, whereupon a clearer sharper image was obtained compared with the case of no coupling medium used.

Field of Utilization in Industry

The coupling medium for a probe of an ultrasonograph according to the present invention is composed of a gel with a high water content and has extremely superior ultrasonographic property and mechanical strength. Further, it uses natural polysaccharides as a raw material, so is high in safety and further is available at low cost in large quantities. Further, an ordinary heat sterilization apparatus can be used, so sterilization is also easy. In addition, the probe coupling medium of the present invention can be directly affixed to the probe of an ultrasonograph using a suitable connection part, so the ease of use is considered to be far more improved compared with those in the past.

We claim:

1. A coupling medium for a probe of an ultrasonograph comprising a gel composing 1–10% by weight of β-1,3 glucan and water.

2. A coupling medium as set forth in claim 1, wherein the concentration of the β-1,3 glucan is 1 to 10% by weight, the sound velocity is 1480 m/s to 1550 m/s, and the attenuation rate is not more than 0.3 dB/MHz•cm.

3. A coupling medium as set forth in claim 3, wherein said β-1,3 glucan is curdlan.

4. A coupling medium as set forth in claim 1, which contains at least one compound selected from the group consisting of sodium or potassium salts of inorganic salts or organic acids, sodium choride, saccharides, and urea.

5. A coupling medium as set forth in claim 1, which contains at least one polymer substance selected from the group consisting of alginic acid, carrageenan, agar—agar, glucomannan, starch, hyaluronic acid, cellulose, methylcellulose, ethylcellulose, nitrocellulose, and polyvinyl alcohols.

6. A coupling medium as set forth in claim 1, wherein said gel is obtained by a high pressure treatment.

7. A coupling medium as set forth in claim 6, wherein the concentration of the β-1,3 glucan is 1 to 10% by weight, the sound velocity is 1480 m/s to 1550 m/s, and the attenuation rate is not more than 0.3 dB/MHz•cm.

8. A coupling medium for a probe of an ultrasonograph as set forth in claim 6, wherein the high pressure treatment condition is at least 100 kg/cm$^2$.

9. A coupling medium as set forth in claim 6, wherein said β-1,3 glucan is curdlan.

10. A coupling medium as set forth in claim 1, wherein at least a portion of the gel is chemically cross-linked.

11. A coupling medium as set forth in claim 10, wherein the concentration of the β-1,3 glucan is 1 to 10% by weight.

12. A coupling medium as set forth in claim 10, wherein the cross-linking agent is contained in an amount of 0.001 to 2% by weight based upon the total weight thereof.

13. A coupling medium as set forth in claim 10, wherein said β-1,3 glucan is curdlan.

14. A coupling medium as set forth in claim 10, wherein said cross-linking agent is at least one cross-linking agent selected from the group consisting of polyhydric glycidylether compounds, polyhydric aziridine compounds, polyhydric amine compounds, polyhydric isocyanate compounds, halomethyl oxirane compounds and aldehydes, and divinyl sulfone.

15. A coupling medium as set forth in claim 1, wherein said gel further contains a complex forming compound which can form a complex with β-1,3 glucan.

16. A coupling medium as set forth in claim 15, wherein the concentration of the β-1,3 glucan is 1 to 10% by weight.

17. A coupling medium as set forth in claim 15, wherein the concentration of the complex forming compound is 5 to 900 mM.

18. A coupling medium as set forth in claim 15, wherein said β-1,3 glucan is curdlan.

19. A coupling medium as set forth in claim 15, wherein the complex forming compound is boric acid.

\* \* \* \* \*